United States Patent
Zou et al.

(10) Patent No.: US 10,719,126 B2
(45) Date of Patent: Jul. 21, 2020

(54) VIRTUAL REALITY GLASSES

(71) Applicant: BOE TECHNOLOGY GROUP CO., LTD., Beijing (CN)

(72) Inventors: Xiangxiang Zou, Beijing (CN); Haoliang Zheng, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/318,151

(22) PCT Filed: May 24, 2018

(86) PCT No.: PCT/CN2018/088146
§ 371 (c)(1),
(2) Date: Jan. 16, 2019

(87) PCT Pub. No.: WO2018/228159
PCT Pub. Date: Dec. 20, 2018

(65) Prior Publication Data
US 2019/0235619 A1    Aug. 1, 2019

(30) Foreign Application Priority Data
Jun. 12, 2017    (CN) .......................... 2017 1 0439819

(51) Int. Cl.
*G06F 3/01*    (2006.01)
*G06F 3/03*    (2006.01)
(Continued)

(52) U.S. Cl.
CPC .............. *G06F 3/012* (2013.01); *A41D 20/00* (2013.01); *A61F 9/027* (2013.01); *G02B 27/0176* (2013.01); *G06F 3/03* (2013.01)

(58) Field of Classification Search
CPC ....... G06F 3/03; G06F 3/012; G02B 27/0176; A41D 20/00; A61F 9/027
See application file for complete search history.

(56) References Cited

U.S. PATENT DOCUMENTS

2014/0022528 A1* 1/2014 Lee ...................... G01S 17/026
                                                                356/4.01
2018/0164594 A1* 6/2018 Lee ..................... G02B 27/0176
(Continued)

FOREIGN PATENT DOCUMENTS

CN    104808772 A    7/2015
CN    204836479 U    12/2015
(Continued)

OTHER PUBLICATIONS

Chinese Office Action in corresponding Chinese Application No. 201710439819.1 dated Jan. 3, 2019 (an English translation attached hereto). 21 pages.

(Continued)

*Primary Examiner* — Liliana Cerullo
(74) *Attorney, Agent, or Firm* — Leason Ellis LLP

(57) ABSTRACT

A virtual reality glasses is disclosed. The virtual reality glasses includes a glasses body, a headband, a drive device and a control device. Two ends of the headband are respectively connected to two ends of the glasses body, and at least one pressure detection device is provided on the headband and/or the glasses body and is configured to detect a pressure applied on a head by at least one of the headband and the glasses body; the drive device is configured to tension and loosen the headband; the control device is configured to communicate with the pressure detection device and the drive device, so as to allow the control device to control the drive device to tension or loosen the headband based on the pressure applied on the head by the at least one of the headband and the glasses body.

20 Claims, 6 Drawing Sheets

(51) Int. Cl.
    *A61F 9/02*     (2006.01)
    *A41D 20/00*     (2006.01)
    *G02B 27/01*     (2006.01)

(56) References Cited

U.S. PATENT DOCUMENTS

| | | | |
|---|---|---|---|
| 2018/0214080 A1* | 8/2018 | Peeters | A61B 5/6831 |
| 2018/0248249 A1* | 8/2018 | Mercer | H01B 19/00 |
| 2019/0101959 A1* | 4/2019 | Fukuma | A61B 5/00 |
| 2019/0159354 A1* | 5/2019 | Zheng | G02B 7/12 |

FOREIGN PATENT DOCUMENTS

| | | |
|---|---|---|
| CN | 205408119 U | 1/2017 |
| CN | 205899145 U | 1/2017 |
| CN | 205910420 U | 1/2017 |
| CN | 205982827 U | 2/2017 |
| CN | 106641667 A | 5/2017 |
| CN | 107179609 A | 9/2017 |

OTHER PUBLICATIONS

International Search Report and Written Opinion in corresponding International Patent Application No. PCT/CN2018/088146, dated Aug. 7, 2018 (an English translation attached hereto). 15 pages.

* cited by examiner

VIRTUAL REALITY GLASSES

CROSS-REFERENCE TO RELATED PATENT APPLICATIONS

This application is a U.S. National Stage Application under 35 U.S.C. § 371 of International Patent Application No. PCT/CN2018/088146, filed May 24, 2018, which claims the benefit of priority under 35 U.S.C. Section 119(e) of Chinese patent application No. 201710439819.1, filed on Jun. 12, 2017, both of which are incorporated herein by reference in their entireties as part of the present application.

TECHNICAL FIELD

Embodiments of the present disclosure relate to a virtual reality glasses.

BACKGROUND

Because virtual reality devices have the advantages of immersion, interaction, imagination and so on, the virtual reality devices have gotten a wide recognition of users and a wide attention of the industry.

SUMMARY

At least one embodiment of the present disclosure provides a virtual reality glasses, and the virtual reality glasses comprises a glasses body, a headband, a drive device and a control device. Two ends of the headband are respectively connected to two ends of the glasses body, and at least one pressure detection device is provided on the headband and/or the glasses body and is configured to detect a pressure applied on a head by at least one of the headband and the glasses body; the drive device is configured to tension and loosen the headband; the control device is configured to communicate with the pressure detection device and the drive device, so as to allow the control device to control the drive device to tension or loosen the headband based on the pressure applied on the head by the at least one of the headband and the glasses body.

For example, in the virtual reality glasses provided by at least one embodiment of the present disclosure, the pressure detection device is located on the headband; the control device is configured to control the drive device to tension the headband in response to a case where the pressure applied on the head by the headband is less than a selected pressure value; the control device is configured to control the drive device to allow the drive device to be powered off and to allow the headband to be kept in a tensioning state in response to a case where the pressure applied on the heard by the headband reaches the selected pressure value.

For example, in the virtual reality glasses provided by at least one embodiment of the present disclosure, the drive device is located on at least one of the two ends of the glasses body and is connected with one of the two ends of the headband.

For example, in the virtual reality glasses provided by at least one embodiment of the present disclosure, the at least one of the two ends of the glasses body is provided with a connection hole, and the one of the two ends of the headband runs through the connection hole and is connected with the drive device.

For example, in the virtual reality glasses provided by at least one embodiment of the present disclosure, a reel is provided on a position, which is adjacent to the connection hole, of the glasses body, the reel is able to be driven by the drive device to rotate, and the one of the two ends of the headband is wound on the reel, so as to allow the headband to be tensioned and loosened.

For example, in the virtual reality glasses provided by at least one embodiment of the present disclosure, the glasses body is provided with a switch for controlling startup and stopping of the drive device.

For example, in the virtual reality glasses provided by at least one embodiment of the present disclosure, the virtual reality glasses further comprises a first sensing device configured to sense a wearing action of the virtual reality glasses. The control device is configured to communicate with the first sensing device so as to control and to start the drive device based on a sensing result of the first sensing device.

For example, in the virtual reality glasses provided by at least one embodiment of the present disclosure, the first sensing device comprises an optical sensor; the first sensing device is arranged at a side, which faces toward the head, of the glasses body, and is configured to detect a distance between the glasses body and the head; the control device is configured to control and start the drive device in a case where the distance, which is detected by the first sensing device, between the glasses body and the head remains constant within a selected time period.

For example, in the virtual reality glasses provided by at least one embodiment of the present disclosure, the virtual reality glasses further comprises a second sensing device configured to sense a position adjustment action of the virtual reality glasses. The control device is configured to communicate with the second sensing device, so as to control the drive device and to allow the drive device to loosen the headband based on a sensing result of the second sensing device.

For example, in the virtual reality glasses provided by at least one embodiment of the present disclosure, the second sensing device comprises an optical sensor; the second sensing device is located on a side, which faces away from the head, of the glasses body, and is configured to detect a distance between the glasses body and a shielding object; the control device is configured to control the drive device and allow the drive device to loosen the headband in a case where the distance, which is detected by the second sensing device, between the glasses body and the shielding object is less than a selected distance.

At least one embodiment of the present disclosure further provides another virtual reality glasses, and the virtual reality glasses comprises a glasses body, a headband, an adjustment-signal supply device and a control device. Two ends of the headband are respectively connected to two ends of the glasses body; the adjustment-signal supply device is configured to provide a headband adjustment signal; the control device is configured to receive the headband adjustment signal, and to adjust an effective working length of the headband based on at least the headband adjustment signal.

For example, another virtual reality glasses provided by at least one embodiment of the present disclosure further comprises a pressure detection device. The pressure detection device is arranged on at least one of the headband and the glasses body, and is configured to detect a pressure applied on a head by at least one of the headband and the glasses body; the adjustment-signal supply device is configured to provide the headband adjustment signal based on at least the pressure applied on the head.

For example, in another virtual reality glasses provided by at least one embodiment of the present disclosure, in a case where the pressure applied on the head is less than a selected pressure value, the adjustment-signal supply device is configured to provide a first headband adjustment signal for reducing the effective working length of the headband; in a case where the pressure applied on the head is equal to the selected pressure value, the adjustment-signal supply device is configured to provide a holding signal for maintaining the effective working length of the headband; in a case where the pressure applied on the head is greater than the selected pressure value, the adjustment-signal supply device is configured to provide a second headband adjustment signal for increasing the effective working length of the headband.

For example, in another virtual reality glasses provided by at least one embodiment of the present disclosure, the control device is further configured to receive an intervention adjustment signal and to adjust the effective working length of the headband based on the headband adjustment signal and the intervention adjustment signal.

For example, another virtual reality glasses provided by at least one embodiment of the present disclosure further comprises at least one of a touch recognition element and a speech recognition element. The touch identification element is configured to provide the intervention adjustment signal based on a touch operation; the speech recognition element is configured to receive and analyze sound, and to provide the intervention adjustment signal based on a sound analysis result.

For example, another virtual reality glasses provided by at least one embodiment of the present disclosure further comprises at least one of a first sensing device and a second sensing device. The first sensing device is configured to sense a wearing action of the glasses, the second sensing device is configured to sense a position adjustment action of the glasses; the adjustment-signal supply device is configured to determine whether or not to provide a first headband adjustment signal for reducing the effective working length of the headband based on at least a sensing result of the wearing action of the glasses; the adjustment-signal supply device is further configured to determine whether or not to provide a second headband adjustment signal for increasing the effective working length of the headband based on at least a sensing result of the position adjustment action of the glasses.

For example, in another virtual reality glasses provided by at least one embodiment of the present disclosure, the at least one of the first sensing device and the second sensing device comprises at least one optical sensor; the first sensing device is located on a side, which faces toward a head, of the glasses body, and is configured to detect a distance between the glasses body and the head, in a case where the distance, which is detected by the first sensing device, between the glasses body and the head remains unchanged within a selected time period, it is determined that the wearing action of the glasses is sensed; the second sensing device is arranged on a side, which faces away from the head, of the glasses body, and is configured to detect a distance between the glasses body and a shielding object, in a case where the distance, which is detected by the second sensing device, between the glasses body and the shielding object is less than a selected distance, it is determined that the position adjustment action of the glasses is sensed.

For example, another virtual reality glasses provided by at least one embodiment of the present disclosure further comprises a drive device, the drive device is configured to adjust the effective working length of the headband under a control of the control device.

For example, another virtual reality glasses provided by at least one embodiment of the present disclosure further comprises a reel. The two ends of the glasses body comprise a first side frame and a second side frame, and the reel is arranged on the first side frame; one of the two ends of the headband is fixed on the reel and the headband is windable around the reel, and the other end of the two ends of the headband is connected to the second side frame; the drive device is configured to adjust a length of the headband wound around the reel under a control of the control device so as to adjust the effective working length of the headband.

For example, in another virtual reality glasses provided by at least one embodiment of the present disclosure, the first side frame is provided with an opening, and the one of the two ends of the headband runs through the opening and is fixed onto the reel.

BRIEF DESCRIPTION OF THE DRAWINGS

In order to clearly illustrate the technical solution of the embodiments of the disclosure, the drawings used in the description of the embodiments or relevant technologies will be briefly described in the following; it is obvious that the described drawings are only related to some embodiments of the disclosure and thus are not limitative of the disclosure.

DETAILED DESCRIPTION

Figure 1:
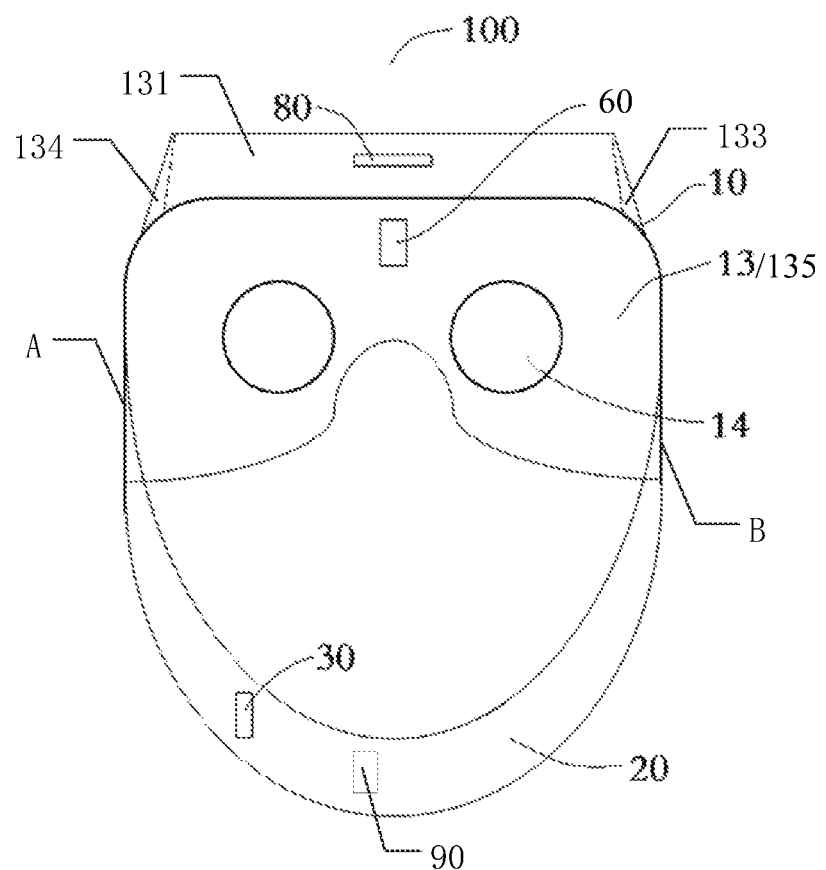
FIG. 1 is a structurally schematic view illustrating a virtual reality glasses according to an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

Current virtual reality glasses usually includes a headband, and require users to manually adjust the tightness of the headband by users themselves, and thus the use experience of users is reduced, especially for users with hand disabilities. The reason for a reduced use experience is that it is necessary for users with hand disabilities to use virtual reality glasses with the help of other persons. Therefore, a kind of virtual reality glasses with autonomous headband adjustment capability is urgently needed.

At least one embodiment of the present disclosure provides a virtual reality glasses, by which, self-adjustment of a headband is achieved, thereby enhancing the use experience of users, especially for users with hand disabilities.

At least one embodiment of the present disclosure provides a virtual reality glasses, and the virtual reality glasses comprises a glasses body, a headband, a drive device and a control device. Two ends of the headband are respectively connected to two ends of the glasses body, and at least one pressure detection device is provided on the headband and/or the glasses body and is configured to detect a pressure applied on a head by at least one of the headband and the glasses body; the drive device is configured to tension and loosen the headband; the control device is configured to communicate with the pressure detection device and the drive device, so as to allow the control device to control the drive device to tension or loosen the headband based on the pressure applied on the head by the at least one of the headband and the glasses body.

At least one embodiment of the present disclosure provides another virtual reality glasses, and the virtual reality glasses comprises a glasses body, a headband, an adjustment-signal supply device and a control device. Two ends of the headband are respectively connected to two ends of the glasses body; the adjustment-signal supply device is configured to provide a headband adjustment signal; the control device is configured to receive the headband adjustment signal, and to adjust an effective working length of the headband based on at least the headband adjustment signal.

For example, in some embodiments, a control device 50 may be configured to control the effective working length of a headband 20 based on at least a headband adjustment signal; in other embodiments, a control device 50 may also be configured to control the effective working length of a headband 20 based on a headband adjustment signal and an intervention adjustment signal, thereby enabling a user to intervene with the headband's autonomous adjustment process.

For example, in some embodiments, the virtual reality glasses may be provided with a pressure detection device so as to detect the pressure that is applied by at least one of the headband and the glasses body on a head, and therefore, the adjustment-signal supply device may be configured to provide the headband adjustment signal based on at least the pressure applied on the head; in another embodiments, the virtual reality glasses may be provided with at least one of a first sensing device and a second sensing device, so as to sense at least one of a wearing action of glasses and a position adjustment action of glasses, and therefore, the adjustment-signal supply device may be configured to be capable of supplying the headband adjustment signal based on at least one of a sensing result of the wearing action of glasses and a sensing result of the position adjustment action of glasses; in still another embodiments, the virtual reality glasses may be provided with all of a pressure detection device, a first sensing device and a second sensing device, thereby enabling the adjustment-signal supply device to provide the headband adjustment signal more intelligently.

Non-limitive descriptions are given to the virtual reality glasses provided by the embodiments of the present disclosure in the following with reference to a plurality of examples. As described in the following, in case of no conflict, different features in these specific examples may be combined so as to obtain new examples, and the new examples are also fall within the scope of present disclosure.

Figure 3:
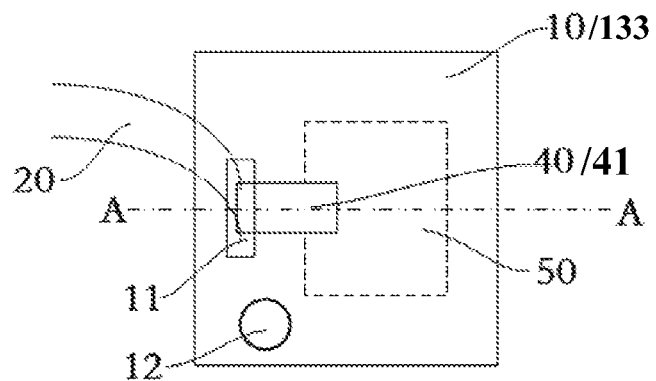
FIG. 3 is a side view of a virtual reality glasses according to an embodiment of the present disclosure.
Figure 4:
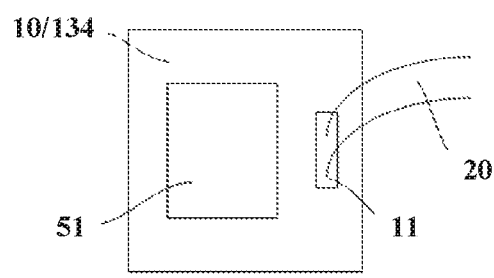
FIG. 4 is another side view of a virtual reality glasses according to an embodiment of the present disclosure.

FIG. 1 is a structurally schematic view of a virtual reality glasses provided by an embodiment of the present disclosure, and FIG. 3 and FIG. 4 are side views of the virtual reality glasses as illustrated in FIG. 1. For example, FIG. 3 and FIG. 4 are images observed from the right side and the left side of FIG. 1, respectively.

As illustrated in FIG. 1 and FIG. 3, the virtual reality glasses 100 according to an embodiment of the present disclosure include a glasses body 10, a headband 20, an adjustment-signal supply device 90, a drive device 40 and a control device 50.

As illustrated in FIG. 1, two ends of the glasses body 10 may include a first side frame 133 and a second side frame 134; two ends of the headband 20 are respectively connected to the two ends of the glasses body 10 (i.e., the first side frame 133 and the second side frame 134 of the glasses body 10). The adjustment-signal supply device 90 is configured to provide a headband adjustment signal; the control device 50 is configured to receive the headband adjustment signal, and to control the drive device 40 and to make the drive device 40 adjust the effective working length of the headband 20 based on at least the headband adjustment signal.

For example, as illustrated in FIG. 1, intersections (or contact points) of the headband 20 with the first side frame 133 and the second side frame 134 are a first point (e.g., point A in FIG. 1) and a second point (e.g., point B in FIG. 1), respectively, and the effective working length of the headband 20 may be the length of the headband 20 between the first point and the second point (between point A and point B). For another example, the effective working length of the headband 20 may also be the length of a portion of the headband in direct contact with a user's head.

For example, in the case where the user is not changed (where the size of the user's head remains unchanged), when the effective working length of the headband 20 increases, the pressure, from the headband and the glasses body 10, as perceived by the user decreases, and in this case, the headband 20 is in a relatively loose state; when the effective working length of the headband 20 decreases, the pressure, from the headband 20 and the glasses body 10, as perceived by the user increases, and in this case, the headband 20 is in a relatively tight state. Thus, in the embodiments of the present disclosure, adjustment of the effective working length of the headband 20 may also be described as tensioning or loosening of the headband 20.

Diverse types of glasses body 10 and headband 20 may be adopted by the embodiments of the present disclosure, and the connection mode between the glasses body 10 and the headband 20 may also be set according to the actual application requirements. For the sake of clarity, the virtual reality glasses 100 provided by an embodiment of the present disclosure may be exemplarily illustrated below based on the glasses body 10, the headband 20 and the connection mode between the glasses body 10 and the headband 20 as illustrated in FIG. 1, but the embodiments of this disclosure are not limited to this case.

Figure 9:
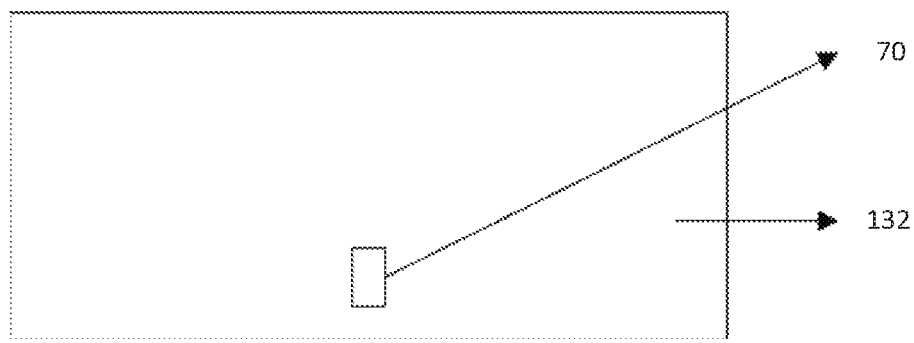
FIG. 9 is a front view of a glasses body provided by an embodiment of the present disclosure.

As illustrated in FIGS. 1 and 9, the glasses body 10 includes a glasses housing 13, which may include an upper frame 131, a front frame 132, a rear frame 135, a first side frame 133 and a second side frame 134. After a user wears the virtual reality glasses 100, the upper frame 131, the front frame 132, the rear frame 135, the first side frame 133 and the second side frame 134 may be all located at the front side of the user's head (face), and the first side frame 133 and the second side frame 134 are positioned at two sides of the user's glasses. As illustrated in FIG. 1, the first side frame 133 and the second side frame 134 may be located at the right side and the left side of the user's eyes, respectively, but the embodiments of this disclosure are not limited to this case. According to the actual application requirements, the first side frame 133 and the second side frame 134 may also be located on the left side and the right side of the user's eyes, respectively. After the user wears the virtual reality glasses 100, as illustrated in FIG. 1, as compared to the front frame 132, the rear frame 135 is closer to the user's head.

As illustrated in FIGS. 3-6, the virtual reality glasses further include a reel 41, which is arranged on a side of the first side frame 133 nearer to the user's head (that is, the side of the first side frame 133 nearer to the second side frame 134), and the drive device 40 (for example, which includes a motor) is connected to the reel 41 and used for driving the reel 41 to rotate. The first side frame 133 is provided with an opening (that is, a connection hole) 11, one end 201 of the headband 20 runs through the opening 11 and is fixed to the reel 41 and moreover the headband 20 can be wound around the reel 41, and the other end of the headband 20 is connected to the second side frame 134. Under the control of the control device 50, the drive device 40 is configured to drive the reel 41 to rotate, so that the length of the headband 20 that is wound around the reel 41 can be adjusted, and therefore, the effective working length of the headband 20 can be adjusted.

Figure 5:
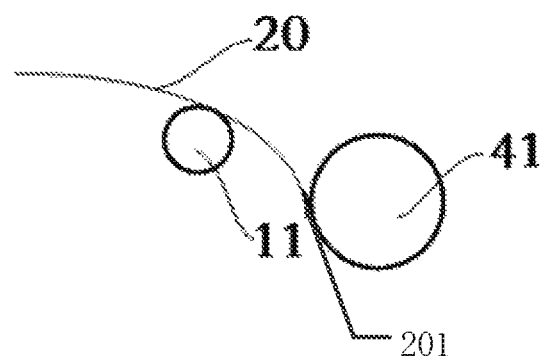
FIG. 5 is a schematic view illustrating a connection between a headband and a reel of a virtual reality glasses according to an embodiment of the present disclosure.
Figure 6:
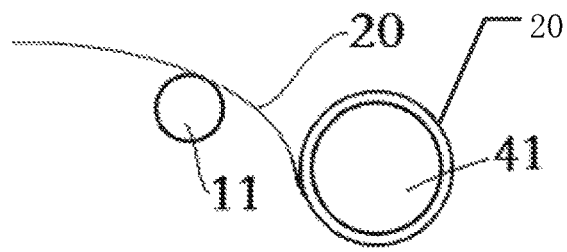
FIG. 6 is another schematic view illustrating a connection between a headband and a reel of a virtual reality glasses according to an embodiment of the present disclosure.

In the case where the virtual reality glasses is in a wearing process (or are not worn), as illustrated in FIG. 5, the length of the headband 20 that is wound around the reel 41 is relatively short; and in this case, the effective working length of the headband 20 is relatively long, the pressure from the headband 20 and the glasses body 10 as perceived by the user is small (or no pressure is perceived), and in this case, the headband 20 is in a relatively loose state. As illustrated in FIG. 6, the length of the headband 20 wound around the reel 41 is relatively long, and therefore, the effective working length of the headband 20 is relatively short, and the pressure from the headband and the glasses body 10 as perceived by the user is relatively large. In this case, the headband 20 is in a relatively tight state, and the virtual reality glasses 100 can be securely worn on the user's head.

For example, the virtual reality glasses may further includes a second reel (not illustrated in the figure), which may be arranged on the side of the second side frame 134 nearer to the first side frame 133, and the second side frame 134 is provided with an opening (i.e., a connection hole) 11. The other end of the headband 20 runs through the opening 11 and is fixed to the second reel, and more over the headband 20 can be wound around the second reel. By provision of the second reel, a longer headband 20 can be provided and the longer headband 20 can be wound around the first reel and the second reel, and thus the adjustment range of the length of the headband 20 can be increased.

In some embodiments, at least one of the first side frame 133 and the second side frame 134 may not be provided with an opening 11. In the case where the first side frame 133 is not provided with an opening 11, the first end 201 of the headband 20 and the reel 41 may be arranged, for example, on the side of the first side frame 133 away from the second side frame 134. In the case where the virtual reality glasses 100 further includes the second reel and the second side frame 134 is not provided with an opening 11, the second reel may be arranged on the side of the second side frame 134 away from the first side frame 133.

Thereinafter, detailed description will be given in connection with FIG. 3 to FIG. 6. As illustrated in FIGS. 3-6, in some embodiments of the present disclosure, the drive device 40 is located at one end of the glasses body 10 (at the right end of the glasses body 10 as illustrated in FIG. 3, that is, on the first side frame 133), and the drive device 40 is connected to the right end (i.e., the first end 201) of the headband 20 (for example, the drive device 40 is connected to the right end of the headband 20 via the reel 41). At either end of the glasses body 10, there is provided a connection hole 11, and two ends of the headband 20 respectively run through corresponding connection holes 11 and are respectively connected with the glasses body 10. At a position of the glasses body 10 nearer to the connecting hole 11 at the right-side (that is, on the first side frame 133), there is arranged a reel 41 which is driven by the drive device 40 to rotate, and one end of the headband 20 is wound on the reel 41. Through rotation of the reel 41, the length of the headband 20 that is wound around the reel 41 is changed, and thus tensioning and loosening of the headband 20 are realized.

According to another embodiment of the present disclosure, one end of the glasses body 10 is fixedly connected to one end of the headband 20, and the connection hole is provided 11 at the other end of the glasses body 10. The reel 411 is provided at the position of the connection hole 11, and the reel 411 is driven by the drive device 40 to rotate. The other end of the headband 20 passes through the connection hole 11 and is wound on the reel 41, and thereby tensioning and loosening of the headband 20 are adjusted by for example adjusting one end of the headband 20.

According to still another embodiment of the present disclosure, both ends of the glasses body 10 are provided with the connection hole 11, and the reel 41 controlled by the drive device 40. Two ends of the headband 20 run through connection holes 11 at corresponding ends, respectively, and are wound on corresponding reels 41. The drive device 40 may drive two reels 41 to rotate, and thereby tensioning and loosening of the headband 20 (that is, the effective working length of the headband 20) are adjusted by adjusting the length of the headband 20 wound around the two reels 41.

As illustrated in FIG. 1, the virtual reality glasses 100 may further include a pressure detection device 30 (e.g., a pressure sensor), which may be arranged on at least one of the headband 20 and the glasses body 10, and is used to detect the pressure of at least one of the headband 20 and the glasses body 10 on the head. For example, the pressure detection device 30 may be arranged on the headband 20, and in this case, the pressure of the headband 20 on the user's head can be sensed by the pressure detection device 30. The pressure detection device 30 may also be arranged on the glasses body 10 (not illustrated in the figure), and in this case, the pressure of the glasses body 10 on the user's head can be sensed by the pressure detection device 30. The headband 20 and the glasses body 10 may be separately provided with at least one pressure detection device 30 as well, and in this case, the pressure detection devices 30 can be used to detect the pressure of the headband 20 and the glasses body 10 on the head, so that the information of the pressure as perceived by the user's head can be obtained more accurately.

The adjustment-signal supply device 90 is configured to provide a headband adjustment signal based on at least the pressure applied on the head. For example, when the pressure applied on the head is less than a selected pressure value (for example, the pressure applied on the head is less than the selected pressure value and greater than zero), the adjustment-signal supply device 90 is configured to provide a first headband adjustment signal for reducing the effective working length of the headband 20. When the pressure applied on the head is equal to the selected pressure value, the adjustment-signal supply device 90 is configured to provide a holding signal for maintaining the effective working length of the headband 20. When the pressure applied on the head is greater than the selected pressure value, the adjustment-signal supply device 90 is configured to provide a second headband adjustment signal for increasing the effective working length of the headband 20.

For example, the selected pressure value may be a pressure range, and the selected pressure value (or the pressure value range) may firstly be set on the basis of the test results before they leave the factory, and then may also be adjusted by the user according to the user's actual use experience. For example, in the case where the selected pressure value is a pressure range, if the pressure applied on the head that is detected by the pressure detection device 30 is greater than the maximum value of the selected pressure value, then it is determined that the pressure applied on the head is greater than the selected pressure value; if the pressure applied on the head that is detected by the pressure detection device 30 is less than the minimum value of the selected pressure value, then it is determined that the pressure applied on the head is less than the selected pressure value; if the pressure applied on the head that is detected by the pressure detection device 30 falls within the selected pressure value range, then it is determined that pressure applied on the head is equal to the selected pressure value.

As illustrated in FIG. 1, in the virtual reality glasses 100 according to an embodiment of the present disclosure, the pressure detection device 30 is arranged on the headband 20. The pressure of the headband 20 on the head is detected by the pressure detection device 30, and thus the tension degree of the headband 20 is controlled according to the pressure of the headband 20 on the head.

In the case where the virtual reality glasses 100 are in a wearing process, when the pressure of the headband 20 on the head is less than the selected pressure value, the adjustment-signal supply device 90 is configured to provide the first headband adjustment signal for reducing the effective working length of the headband 20. The control device 50 receives the first headband adjustment signal, and make the drive device 40 operate under its control so as to reduce the effective working length of the headband 20, thereby the head band 20 is tensioned. When the pressure of the headband 20 on the head reaches the selected pressure value, the adjustment-signal supply device 90 is configured to provide a holding signal for maintaining the effective working length of the headband 20, and the control device 50 receives the holding signal and allows the drive device 40 to be powered off by controlling, so that the headband 20 is kept in a tensioning state. Thus, the virtual reality glasses 100 are worn on the head securely and comfortably.

In the virtual reality glasses 100 according to another embodiment of the present disclosure, the pressure detection device 30 may be arranged on the glasses body 10. The pressure of the glasses body 10 on the head is detected by the pressure detection device 30, and the adjustment-signal supply device 90 is configured to provide the headband adjustment signal (e.g., the first headband adjustment signal, the second headband adjustment signal or the holding signal) based on at least the pressure of the glasses body 10 on the head. The control device 50 receives the headband adjustment signal, and make the drive device 40 operate under its control based on the headband adjustment signal, thereby adjusting the effective working length of the headband 20 and controlling the tension degree of the headband 20.

For example, in some embodiments of the present disclosure, the adjustment-signal supply device 90 may be arranged in the pressure detection device 30 and act as a component of the pressure detection device 30, and in this case, the control device 50 may communicate directly with the pressure detection device 30. In some embodiments of the present disclosure, it is configured in such a way that the control device 50 is configured to communicate with the pressure detection device 30 and the drive device 40 when the virtual reality glasses 100 is in operation, so that tensioning or loosening of the headband 20 by the drive device 40 can be controlled on the basis of the value of pressure(s) that is/are applied by the headband 20 and/or the glasses body 10 on the head.

For example, in the virtual reality glasses 100 provided by some embodiments of the present disclosure, the control device 50 cooperates with the pressure detection device 30, to allow the drive device 40 to tension or loosen the headband 20 under its control, and thereby intelligent control can be realized. Consequently, the tightness of the headband 20 can be adjusted automatically and in real time according to wearing condition, and the problem of use inconvenience for disabled persons is solved with good effect.

Figure 2:
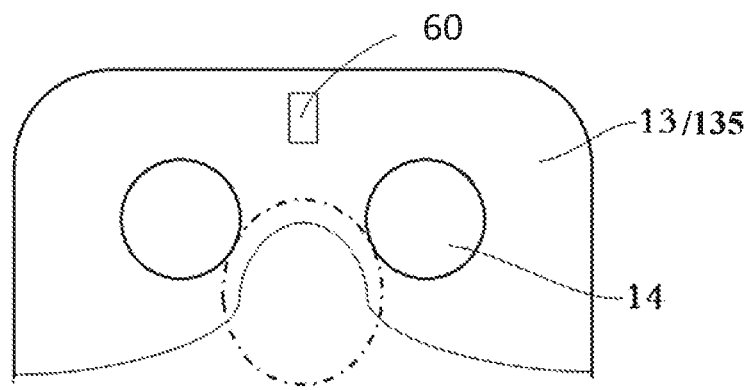
FIG. 2 is a structurally schematic view illustrating a side, which faces toward a head, of a virtual reality glasses according to an embodiment of the present disclosure.
Figure 10:
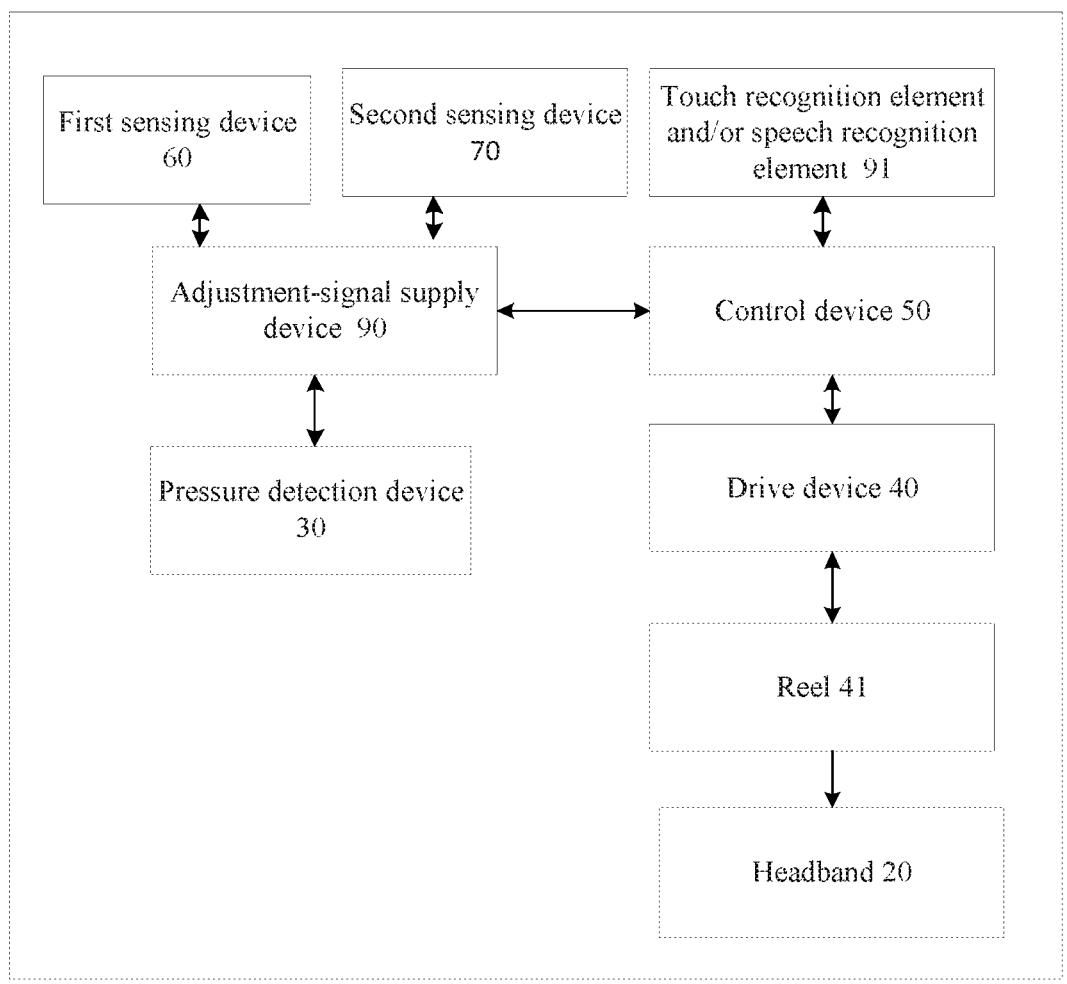
FIG. 10 is an exemplary block diagram of a virtual reality glasses provided by an embodiment of the present disclosure.

In some embodiments of the present disclosure, the virtual reality glasses 100 further includes at least one of a first sensing device 60 and s second sensing device 70. The first sensing device 60 is used to sense a wearing action of the glasses, and the second sensing device 70 is used to sense a position adjustment action of the glasses (e.g. a removing action of the glasses). The adjustment-signal supply device 90 is configured to determine whether or not to provide the first headband adjustment signal for reducing the effective working length of the headband 20 based on at least the sensing result of wearing action of the glasses (see FIG. 10). The adjustment-signal supply device 90 is further configured to determine whether or not to provide the second headband adjustment signal for increasing the effective working length of the headband 20 based on at least the sensing result of position adjustment action of the glasses. Exemplary illustrations will be given below in conjunction with FIGS. 1 to 2 and FIG. 9.

As illustrated in FIG. 1, in some embodiments of the present disclosure, the virtual reality glasses 100 further includes a first sensing device 60 capable of sensing a wearing action of the virtual reality glasses 100, and the first sensing device 60 may be provided with an adjustment-signal supply device 90. In this case, the control device 50 is configured to communicate with the first sensing device 60, and thus the control device 50 can control the working state (e.g., rotating or maintaining immobility) of the drive device 40 based on the sensing result of the first sensing device 60.

For example, the first sensing device 60 is arranged on the side of the glasses body 10 facing toward the head (that is, it is arranged on the side of the rear frame 135 away from the front frame 132), and is used to detect the distance (the distance along the horizontal direction) between the glasses body 10 (e.g., the rear frame 135) and the user's head. For example, the first sensing device 60 may include at least one optical sensor (e.g., an infrared distance sensor or a laser rangefinder), and the optical sensor is used to measure related parameters according to optical principles, and can be useful for detecting the distance between the glasses body 10 and the head.

When the distance between the glasses body 10 and the head that is detected by the first sensing device 60 remains constant within a selected time period, it is determined that a wearing action is conducted (that is, it is determined that a wearing action of the glasses is sensed). In this case, the adjustment-signal supply device 90 is configured to provide the first headband adjustment signal for reducing the effective working length of the headband 20. Thus, the control device 50 makes the drive device 40 start up under its control, and then the drive device 40 drives the reel 41 to rotate (for example, the drive device 40 rotates the reel counterclockwise), so that the effective working length of the headband 20 is reduced and the headband 20 is tensioned to complete the wearing action.

It should be noted that, the above-mentioned method of determination of the wearing action of glasses may be combined with other methods so as to improve the accuracy of determination result of the wearing action of glasses. For example, it may be determined that a wearing action of glasses is sensed and thus the pressure detection device 30 is triggered and allowed to be in the working state in the case where the detected distance between the glasses body 10 and the head decreases gradually at first and then the detected distance remains constant during the selected time period. For another example, the pressure detection device 30 may be started up in the case where the detected distance between the glasses body 10 and the head remains constant, and then, it is determined that a wearing action of the glasses is sensed in the case where the pressure applied on the head detected by the pressure detection device 30 is less than the selected pressure value.

It is determined that a wearing action of the glasses is not sensed when it is not detected by the first sensing device 60 that the distance between the glasses body 10 and the head is unchanged within the selected time period. In this case, the adjustment signal supply device 90 is configured to provide the holding signal, so as to keep the effective working length of the headband 20 unchanged.

For example, by provision of the first sensing device 60, it is possible to avoid misjudging the case where the virtual reality glasses 100 are not worn as a wearing action or failing to trigger operation of the drive device 40 at the initial time of wearing. Consequently, the use experience of the virtual reality glasses 100 can be promoted.

For example, the technical solution that intelligent control of the length of the headband 20 by adopting optical sensors to detect a wearing action has the advantages of simple structure, low cost, high sensitivity and good user experience.

As illustrated in FIG. 9, in some other embodiments of the present disclosure, the virtual reality glasses 100 may further include a second sensing device 70, which is used for sensing a position adjustment action of the virtual reality glasses 100 (e.g. a glasses removal action). The second sensing device 70 is disposed at the side of the glasses body 10 away from the head (e.g., the second sensing device 70 is disposed at the side of the front frame 132 away from the rear frame 135). The second sensing device 70 may include at least one optical sensor (e. g., an infrared distance sensor or a laser rangefinder), but the embodiments of this disclosure are not limited to this case.

The second sensing device 70 may be used to detect the distance between the glasses body 10 (e.g. a front frame 132) and a shielding object (e.g. a light shielding facet or a palm). For example, it is determined that an action, indicating that position adjustment of the glasses (e.g., an action of removing the glasses) is need, is conducted, in the case where emerging of the shielding object is detected by the second sensing device 70 (e.g., when a user lowers his head and this causes the second sensing device 70 to face a tabletop between his legs and head), and the distance between the shielding object and the second sensing device 70 is less than the selected distance. In this case, the adjustment-signal supply device 90 is configured to provide the second headband adjustment signal for increasing the effective working length of the headband 20, and thereby the control device 50 makes the drive device rotate the reel 41 (e.g., the control device 50 rotates the reel clockwise) under its control, so as to increase the effective working length of headband 20 and to loosen the headband 20.

It should be noted that, the embodiments of the present disclosure are not limited to the case where it is determined that a position adjustment action of glasses is sensed when the distance between a shielding object (not illustrated in the figure) and the glasses body 10 is less than the selected distance. According to the actual application requirements, when the distance between the glasses body 10 and a shielding object decreases continuously, it may also be determined that a position adjustment action of glasses is sensed. For another example, it may also be determined that a position adjustment action of glasses has been sensed when the distance between the glasses body 10 and a shielding object decreases continuously until the distance between the shielding object and the glasses body 10 reaches the selected distance.

Figure 11:
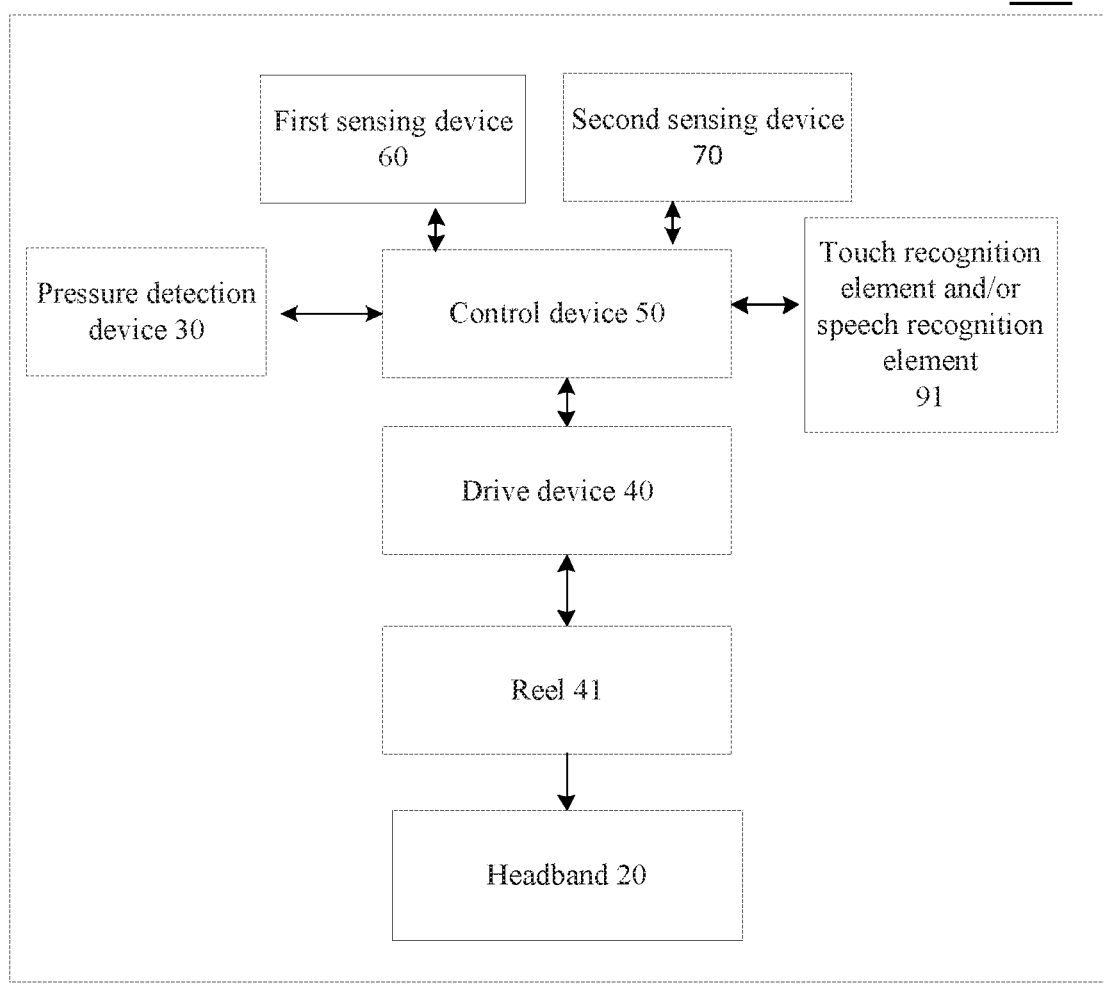
FIG. 11 is an exemplary block diagram of another type of virtual reality glasses provided by an embodiment of the present disclosure.

It should be noted that, the adjustment-signal supply device 90 is not limited to be arranged in a position different from the pressure detection device 30, the first sensing device 60 and the second sensing device 70, and according to the actual application requirements, the adjustment-signal supply device 90 may be arranged in at least one of the pressure detection device 30, the first sensing device 60 and the second sensing device 70. In this case, the control device 50 may communicate directly with at least one of the pressure detection device 30, the first sensing device 60 and the second sensing devices 70 (see FIG. 11), so as to make the drive device 40 adjust the length of the headband 20 under its control in accordance with at least one of sensing results of the pressure detection device 30, the first sensing device 60 and the second sensing device 70.

For example, in the case where the virtual reality glasses 100 includes all of the pressure detection device 30, the first sensing device 60 and the second sensing device 70, and the virtual reality glasses 100 includes three adjustment-signal supply devices 90 arranged in the pressure detection device 30, the first sensing device 60 and the second sensing device 70, respectively, the three adjustment-signal supply devices 90 can communicate with each other.

It should be noted that, in the case where the virtual reality glasses 100 include all of the pressure detection device 30, the first sensing device 60 and the second sensing device 70, the adjustment-signal supply device 90 can provide the headband adjustment signal based on the combination of the sensing results of the pressure detection device 30, the first sensing device 60 and the second sensing device 70.

For example, when the distance between the glasses body 10 and the head detected by the first sensing device 60 remains constant within the selected time period and the pressure applied on the head detected by the pressure detection device 30 is less than the selected pressure value, it is determined that a wearing action of glasses is sensed. The adjustment-signal supply device 90 provides a first headband adjustment signal to reduce the effective working length of the headband 20, until the pressure applied on the head detected by the pressure detection device 30 is equal to the selected pressure value, and then, the adjustment-signal supply device 90 provides a holding signal, so as to keep the effective working length of the headband 20 unchanged.

For another example, when the distance between the glasses body 10 and the head detected by the first sensing device 60 remains constant within the selected time period, but the pressure applied on the head detected by the pressure detection device 30 is equal to the selected pressure value, it is determined that a wearing action of glasses is sensed. In this case, the adjustment-signal supply device 90 provides a holding signal, so as to keep the effective working length of the headband 20 unchanged.

For example, the virtual reality glasses 100 may further include at least one of a touch recognition element and a speech recognition element 91. The touch recognition element is configured to provide an intervention adjustment signal based on the user's touch operation; and the speech recognition element 91 is configured to receive and analyze sound, and to provide an intervention adjustment signal based on the sound analysis result. In this case, the control device 50 is further configured to receive the intervention adjustment signal(s) and to control the effective working length of the headband 20 based on the headband adjustment signal and the intervention adjustment signal(s).

By means of letting the control device 50 control the effective working length of headband 20 based on the headband adjustment signal and the intervention adjustment signal(s), the user is allowed to intervene with the headband automatic adjustment process. Consequently, the user's experience can be further promoted.

For example, the touch recognition element may be implemented as a start-stop button or a touch panel. For example, the start-stop button or the touch panel may include buttons or touch options corresponding to increasing, maintaining, and decreasing of the effective working length of the headband 20. In addition, depending on the actual application requirements, the start-stop button or the touch panel may further include buttons or touch options corresponding to increasing and decreasing of the headband adjusting speed. Exemplary illustrations will be given below in conjunction with FIGS. 3 and 4.

As illustrated in FIG. 4, an end of the glasses body 10 is provided with a control panel 51, and the control panel 51 may be arranged, for example, on the side of the second side frame 134 away from the first side frame 133. The control panel 51 may take control of display of the display screen, and the control panel 51 may also be used for controlling the operation of the display screen after the glasses is worn. Thus, functions such as selecting, playing, stopping, headband adjusting can be performed and different needs of the users can be satisfied. This makes utilization of the virtual reality glasses 100 more intelligent and convenient.

As illustrated in FIG. 3, in some embodiments of the present disclosure, on the glasses body 10 (e.g., on the side of the first side frame 133 away from the second side frame 134), there is also provided a switch 12 for controlling startup and stopping of the drive device 40. Thus, when the pressure detection device 30 is disabled, startup and stopping of the drive device 40 may be controlled directly by the switch 12, and therefore, the control is more convenient.

In some embodiments of the present disclosure, the virtual reality glasses 100 may further include a speech control device (not illustrated in the figure), and the speech control device may include a speech recognition element 91, which may include a microphone, a speech feature extraction module and a pattern matching module. In this case, the speech feature extraction module and the pattern matching module may respectively include a processor and a memory, and regarding the concrete implementing mode of the processor and memory, other examples can be referred, details are omitted here. For example, the speech control device may be used to identify the speech information inputted by a user, and by means of communicating the control device 50 with the speech control device, tensioning and loosening of the headband 20 can be controlled by the speech information. Furthermore, all kinds of operations with respect to a display screen can also be realized after the glasses is worn, and this makes the virtual reality glasses 100 more intelligent and improves the user's use experience. In addition, various problems encountered by disabled persons upon their own use of the virtual display glasses 100 can be solved with good effect as well.

For example, the adjustment-signal supply device 90 and the control device 50 may respectively include a processor and a memory, and the processor is, for example, a central processing unit (CPU) or other processing unit having data processing capabilities and/or instruction executing capabilities. For example, the processor may be implemented as a general-purpose processor, and may also be a single-chip microcomputer, a microprocessor, a digital signal processor, a dedicated image processing chip, a field programmable logic array, or the like. The memory may, for example, include a volatile memory and/or a non-volatile memory, and for example, the memory may include a read-only memory (ROM), a hard disk, a flash memory, etc. Accordingly, the memory may be implemented as one or more computer program products, which may include computer readable storage media in various forms, on which one or more computer program instructions may be stored. The program instructions can be operated on by the processor, so as to implement function of the control device and/or other desired functions in the embodiments of the disclosure as described below, and various other application programs and various data (e.g., the detected pressure applied on the head that is outputted from the pressure detection device 30) may also be stored in the memory.

For example, the pressure detection device may be a pressure sensor based on diverse physical principles of elasticity, electrification or the like. For example, the pressure detection device may be a spring tube pressure gauge, a bellows-type pressure gauge, a resistance strain pressure sensor, a capacitive pressure sensor, a piezoelectric pressure sensor, and so on.

For example, the drive device may be a drive motor based on a variety of power sources, such as a pneumatic actuator, a hydraulic actuator, an electric actuator, an electromagnetic actuator, a thermal actuator, a MEMS actuators, and so on.

It should be noted that, as for any other component of the adjustment-signal supply device 90 and the control device 50 (e.g., a signal transmitting element or a signal receiving element), suitable components may be adopted. This should be understood by those ordinary skilled in the art, and will not be discussed here, and it should not be construed as limiting of the embodiments of the disclosure.

For example, the following transmission of signals and/or instructions between devices and/or elements may be achieved by physical lines between each other, or by a communication device (not illustrated in the figure) in a wired or wireless manner transmission of signals and/or instructions between the pressure detection device 30 and the adjustment-signal supply device 90, between the first sensing device 60 and the adjustment-signal supply device 90, and between the second sensing device 70 and the adjustment-signal supply device 90; transmission of signals and/or instructions between the adjustment-signal supply device 90 and the control device 50; transmission of signals and/or instructions between the touch recognition element and/or the speech recognition element 91 and the control device 50; and transmission of signals and/or instructions between the control device 50 and the drive device 40. For example, the communication device may communicate with other devices (such as personal computers, servers, mobile stations, base stations, etc.) via network technologies or other technologies. The network may be an internet, a wireless local area network, a mobile communication network, or the like, and the other technology may include, for example, Bluetooth communication technology, infrared communication technology, or the like.

As illustrated in FIG. 1, in some embodiments of the present disclosure, the virtual reality glasses 100 may further be provided with (e.g., two) optical lenses 14 and a display screen (not illustrated in the figure), the two optical lenses 14 are arranged side by side in the glasses housing 13, and the display screen is located at the front side of the two optical lenses 14 (e.g., the display screen is located between the optical lens 14 and the front frame 132). On the glasses housing 13, there is provided a focus adjusting device 80, by which, the distance between the display screen and the optical lens 14 can be adjusted (e.g., the focus adjusting device 80 may include a motor), thus enabling the display screen to be located at the focuses of the optical lens 14 (for example, enabling of the display screen to be located at the focuses of the optical lens 14 may be achieved by rotating the focus adjusting device 80).

Figure 7:
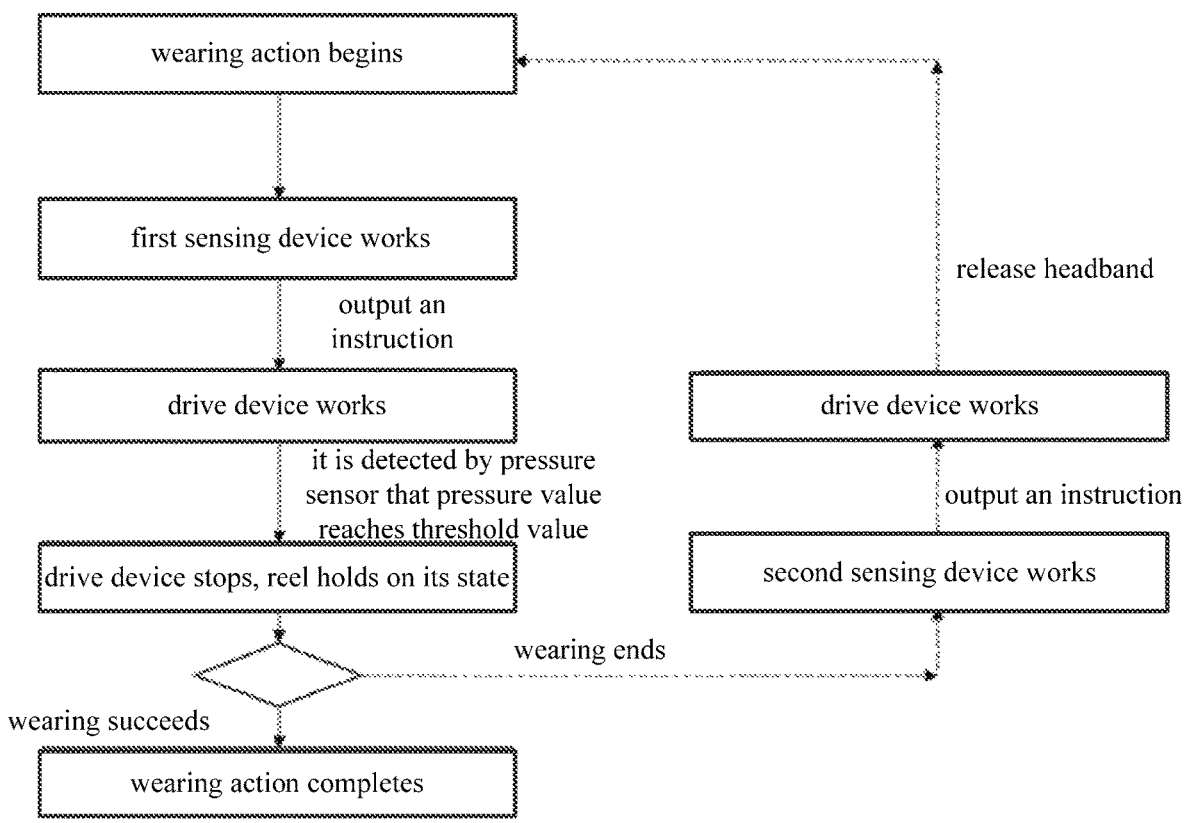
FIG. 7 is an exemplary flowchart illustrating wearing of a virtual reality glasses according to an embodiment of the present disclosure.
Figure 8:
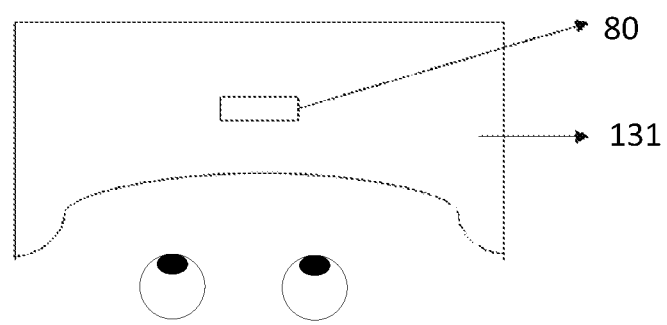
FIG. 8 is a top view of a glasses body provided by an embodiment of the present disclosure.

The concrete process of wearing and removing the virtual reality glasses 100 according to an embodiment of the present disclosure will be described below in conjunction with FIG. 7.

When it is detected by the optical sensor of the first sensing device 60 that the distance between the glasses body 10 and the head has a tendency to decrease, or when it is detected by the optical sensor that the distance between the glasses body 10 and the head remains constant within the selected time period, it is determined that a wearing action is sensed. In this case, the adjustment-signal supply device 90 provides the control device 50 with a first headband adjustment signal for reducing the effective working length of the headband 20 (alternatively, the first sensing device 60 outputs a wearing signal and transmits it to the control device 50), and thus the control device 50 makes the drive device 40 operate under its control, so as to allow the reel 41 to start rotating. The reel 41 rotates to tighten the headband 20 (that is, to reduce the effective working length of the head band 20), and the pressure detection device 30 on the head band 20 is kept in operation. When the pressure value detected by the pressure detection device 30 exceeds a selected threshold (that is, the selected pressure value), the adjustment-signal supply device 90 (or the first sensing device 60) provides a holding signal to the control device 50, so as to allow the drive device 40 to stop working. The reel 41 stops rotating and the effective working length of the headband 20 maintains unchanged, thereby completing the wearing process.

When it is detected by the optical sensor of the second sensing device 70 that there is emergence of a shielding object, and the distance between the glasses body and the shielding object is less than the selected distance and/or the distance between the glasses body 10 and the shielding object continues to decrease until it reaches the selected distance, it is determined that this is an action indicating position adjustment of the glasses (for example, an action of removing the glasses) is needed. In this case, a position adjustment signal is outputted and sent to the control device 50. The control device 50 makes the drive device 40 operate under its control, and thus the reel 41 is allowed to rotate (e.g., it rotates counterclockwise), so as to release the headband 20. By this way, a user can remove the virtual reality glasses 100 with ease.

In addition, the virtual reality glasses 100 may further include at least one power supply, which can supply power to various components (e.g., the drive device 40, the control device 50, the adjustment-signal supply device, etc.) of the virtual reality glasses 100.

It should be noted that other components (for example, an image data encoding/decoding device, a row scan driver, a column scan driver, a clock circuit and so on) of the virtual reality glasses 100 may adopt conventional components, this should be understood by those skilled in the art, no further descriptions will be given herein and it should not be construed as a limitation on the embodiments of the present disclosure.

Although detailed description has been given above to the present disclosure with general description and embodiments, it shall be apparent to those skilled in the art that some modifications or improvements may be made on the basis of the embodiments of the present disclosure. Therefore, all the modifications or improvements made without departing from the spirit of the present disclosure shall all fall within the scope of protection of the present disclosure.

What are described above is related to the illustrative embodiments of the disclosure only and not limitative to the scope of the disclosure; the scopes of the disclosure are defined by the accompanying claims.

What is claimed is:

1. A virtual reality glasses, comprising:
    a glasses body;
    a headband, wherein two ends of the headband are respectively connected to two ends of the glasses body, and at least one pressure detection device is provided on at least one of the headband and the glasses body and is configured to detect a pressure applied on a head by at least one of the headband and the glasses body;
a drive device, wherein the drive device is configured to tension and loosen the headband;
a controller,
wherein the controller is configured to communicate with the pressure detection device and the drive device, so as to allow the controller to control the drive device to tension or loosen the headband based on the pressure applied on the head by the at least one of the headband and the glasses body;
the pressure detection device is located on the headband;
the controller is configured to control the drive device to tension the headband in response to a case where the pressure applied on the head by the headband is less than a selected pressure value; and
the controller is configured to control the drive device to allow the drive device to be powered off and to allow the headband to be kept in a tensioning state in response to a case where the pressure applied on the head by the headband reaches the selected pressure value.

2. The virtual reality glasses according to claim 1, wherein the drive device is located on at least one of the two ends of the glasses body and is connected with one of the two ends of the headband.

3. The virtual reality glasses according to claim 2, wherein the at least one of the two ends of the glasses body is provided with a connection hole, and the one of the two ends of the headband runs through the connection hole and is connected with the drive device.

4. The virtual reality glasses according to claim 3, wherein a reel is provided on a position, which is adjacent to the connection hole, of the glasses body, the reel is able to be driven by the drive device to rotate, and the one of the two ends of the headband is wound on the reel.

5. The virtual reality glasses according to claim 1, wherein the glasses body is provided with a switch for controlling startup and stopping of the drive device.

6. The virtual reality glasses according to claim 1, further comprising a first sensing device configured to sense a wearing action of the virtual reality glasses,
wherein the controller is configured to communicate with the first sensing device so as to control and to start the drive device based on a sensing result of the first sensing device.

7. The virtual reality glasses according to claim 6, wherein the first sensing device comprises an optical sensor;
the first sensing device is arranged at a side, which faces toward the head, of the glasses body, and is configured to detect a distance between the glasses body and the head; and
the controller is configured to control and start the drive device in a case where the distance, which is detected by the first sensing device, between the glasses body and the head remains constant within a selected time period.

8. The virtual reality glasses according to claim 6, further comprising a second sensing device configured to sense a position adjustment action of the virtual reality glasses,
wherein the controller is configured to communicate with the second sensing device, so as to control the drive device and to allow the drive device to loosen the headband based on a sensing result of the second sensing device.

9. The virtual reality glasses according to claim 8, wherein the second sensing device comprises an optical sensor;

the second sensing device is located on a side, which faces away from the head, of the glasses body, and is configured to detect a distance between the glasses body and a shielding object; and
the controller is configured to control the drive device and allow the drive device to loosen the headband in a case where the distance, which is detected by the second sensing device, between the glasses body and the shielding object is less than a selected distance.

10. A virtual reality glasses, comprising: a glasses body, a headband, a reel, an adjustment-signal supplier, a drive device and a controller,
wherein two ends of the headband are respectively connected to two ends of the glasses body;
the adjustment-signal supplier is configured to provide a headband adjustment signal;
the controller is configured to receive the headband adjustment signal, and to adjust an effective working length of the headband based on at least the headband adjustment signal;
the two ends of the glasses body comprise a first side frame and a second side frame, and the reel is arranged on the first side frame;
one of the two ends of the headband is fixed onto the reel and the headband is windable around the reel, and the other end of the two ends of the headband is connected to the second side frame; and
the drive device is configured to adjust a length of the headband wound around the reel under a control of the controller so as to adjust the effective working length of the headband.

11. The virtual reality glasses according to claim 10, further comprising a pressure detection device,
wherein the pressure detection device is arranged on at least one of the headband and the glasses body, and is configured to detect a pressure applied on a head by at least one of the headband and the glasses body; and
the adjustment-signal supplier is configured to provide the headband adjustment signal based on at least the pressure applied on the head.

12. The virtual reality glasses according to claim 11, wherein in a case where the pressure applied on the head is less than a selected pressure value, the adjustment-signal supplier is configured to provide a first headband adjustment signal for reducing the effective working length of the headband;
in a case where the pressure applied on the head is equal to the selected pressure value, the adjustment-signal supplier is configured to provide a holding signal for maintaining the effective working length of the headband; and
in a case where the pressure applied on the head is greater than the selected pressure value, the adjustment-signal supplier is configured to provide a second headband adjustment signal for increasing the effective working length of the headband.

13. The virtual reality glasses according to claim 10, wherein the controller is further configured to receive an intervention adjustment signal and to adjust the effective working length of the headband based on the headband adjustment signal and the intervention adjustment signal.

14. The virtual reality glasses according to claim 13, further comprising: at least one of a touch recognition element and a speech recognition element,
wherein the touch identification element is configured to provide the intervention adjustment signal based on a touch operation; and the speech recognition element is configured to receive and analyze sound, and to provide the intervention adjustment signal based on a sound analysis result.

15. The virtual reality glasses according to claim 10, further comprising: at least one of a first sensing device and a second sensing device,
   wherein the first sensing device is configured to sense a wearing action of the glasses, and the second sensing device is configured to sense a position adjustment action of the glasses;
   the adjustment-signal supplier is configured to determine whether or not to provide a first headband adjustment signal for reducing the effective working length of the headband based on at least a sensing result of the wearing action of the glasses; and
   the adjustment-signal supplier is further configured to determine whether or not to provide a second headband adjustment signal for increasing the effective working length of the headband based on at least a sensing result of the position adjustment action of the glasses.

16. The virtual reality glasses according to claim 15, wherein the at least one of the first sensing device and the second sensing device comprises at least one optical sensor;
   the first sensing device is located on a side, which faces toward a head, of the glasses body, and is configured to detect a distance between the glasses body and the head, in a case where the distance, which is detected by the first sensing device, between the glasses body and the head remains unchanged within a selected time period, it is determined that the wearing action of the glasses is sensed; and
   the second sensing device is arranged on a side, which faces away from the head, of the glasses body, and is configured to detect a distance between the glasses body and a shielding object, in a case where the distance, which is detected by the second sensing device, between the glasses body and the shielding object is less than a selected distance, it is determined that the position adjustment action of the glasses is sensed.

17. The virtual reality glasses according to claim 10, wherein the first side frame is provided with an opening, and the one of the two ends of the headband runs through the opening and is fixed onto the reel.

18. A virtual reality glasses, comprising: a glasses body, a headband, a reel, an adjustment-signal supplier, a drive device, a first sensing device and a controller,
   wherein two ends of the headband are respectively connected to two ends of the glasses body;
   the adjustment-signal supplier is configured to provide a headband adjustment signal;
   the controller is configured to receive the headband adjustment signal, and to adjust an effective working length of the headband based on at least the headband adjustment signal;
   the first sensing device is configured to sense a wearing action of the glasses;
   the adjustment-signal supplier is configured to determine whether or not to provide a first headband adjustment signal for reducing the effective working length of the headband based on at least a sensing result of the wearing action of the glasses; and
   the first sensing device is located on a side, which faces toward a head, of the glasses body, and is configured to detect a distance between the glasses body and the head, in a case where the distance, which is detected by the first sensing device, between the glasses body and the head remains unchanged within a selected time period, it is determined that the wearing action of the glasses is sensed.

19. The virtual reality glasses according to claim 18, further comprising: a second sensing device,
   wherein the second sensing device is configured to sense a position adjustment action of the glasses;
   the adjustment-signal supplier is further configured to determine whether or not to provide a second headband adjustment signal for increasing the effective working length of the headband based on at least a sensing result of the position adjustment action of the glasses; and
   the second sensing device is arranged on a side, which faces away from the head, of the glasses body, and is configured to detect a distance between the glasses body and a shielding object, in a case where the distance, which is detected by the second sensing device, between the glasses body and the shielding object is less than a selected distance, it is determined that the position adjustment action of the glasses is sensed.

20. The virtual reality glasses according to claim 19, wherein the at least one of the first sensing device and the second sensing device comprises at least one optical sensor.

* * * * *